United States Patent
Nanthakumar

(10) Patent No.: US 11,123,328 B2
(45) Date of Patent: Sep. 21, 2021

(54) DANTROLENE AND ANALOGS THEREOF FOR THE CHRONIC TREATMENT AND PREVENTION OF DYSSYNCHRONOUS CARDIAC DYSFUNCTION

(71) Applicant: UNIVERSITY HEALTH NETWORK, Toronto (CA)

(72) Inventor: Kumaraswamy Nanthakumar, Toronto (CA)

(73) Assignee: University Health Network, Toronto (CA)

( * ) Notice: Subject to any disclaimer, the term of this patent is extended or adjusted under 35 U.S.C. 154(b) by 0 days.

(21) Appl. No.: 16/763,914

(22) PCT Filed: Nov. 14, 2018

(86) PCT No.: PCT/CA2018/051443
§ 371 (c)(1),
(2) Date: May 13, 2020

(87) PCT Pub. No.: WO2019/095056
PCT Pub. Date: May 23, 2019

(65) Prior Publication Data
US 2020/0375951 A1    Dec. 3, 2020

Related U.S. Application Data

(60) Provisional application No. 62/585,983, filed on Nov. 14, 2017.

(51) Int. Cl.
*A61K 31/4166* (2006.01)
*A61P 9/04* (2006.01)
*A61K 31/4178* (2006.01)
*A61K 31/422* (2006.01)
*A61K 9/00* (2006.01)

(52) U.S. Cl.
CPC ........ *A61K 31/4178* (2013.01); *A61K 31/422* (2013.01); *A61K 9/0019* (2013.01)

(58) Field of Classification Search
CPC .............................. A61K 31/4166; A61P 9/04
USPC ....................................................... 514/390
See application file for complete search history.

(56) References Cited

U.S. PATENT DOCUMENTS

| 4,543,359 A | 9/1985 | Ellis et al. |
| 9,636,327 B2 | 5/2017 | Nanthakumar |

FOREIGN PATENT DOCUMENTS

| WO | 94/05287 A1 | 3/1994 |
| WO | 2014/191837 A2 | 12/2014 |

OTHER PUBLICATIONS

Li H., et al. Cardiac Resynchronization Therapy Reduces Subcellular Heterogeneity of Ryanodine Receptors, T-Tubules, and Ca2+ Sparks Produced by Dyssynchronous Heart Failure. Circ Heart Fail., 2015; 8:1105-1114.
Aiba T., et al. Electrophysiological consequences of dyssynchronous heart failure and its restoration by resynchronization therapy. Circulation, 2009; 119:1220-1230.
Gangopadhyay J. P., et al. Intracellular translocation of calmodulin and Ca2+/calmodulin-dependent protein kinase II during the development of hypertrophy in neonatal cardiomyocytes. Biochem Biophys Res Commun, 396, 2010, 515-521.
Zamiri N., et al. Dantrolene improves survival after ventricular fibrillation by mitigating impaired calcium handling in animal models. Circulation. 2014; 129:875-885.
Mariani J. A., et al. Augmentation of left ventricular mechanics by recirculation-mediated AAV2/1-SERCA2a gene in delivery experimental heart failure. Eur J Pharmacol. 2011, 13, 247-253.
Hanna A. D., et al. Adverse Effects of Doxorubicin and Its Metabolic Product on Cardiac RyR2 and SERCA2A. Mol Pharmacol. Oct. 2014; 86(4): 438-449.
Fischer T. H., et al. Ca2+/calmodulin-dependent protein kinase II and protein kinase A differentially regulate sarcoplasmic reticulum Ca2+ leak in human cardiac pathology. Circulation 2013;128:970-981.
Dewenter M., et al. Calcium/calmodulin-dependent protein kinase II activity persists during chronic beta-adrenoceptor blockade in experimental and human heart failure. Circ Heart Fail 2017;10(5):e003840.
Kobayashi S., et al. Dantrolene, a therapeutic agent for malignant hyperthermia, markedly improves the function of failing cardiomyocytes by stabilizing inter-domain interactions within the ryanodine receptor. J Am Coll Cardiol 2009;53:1993-2005.
Walweel, K., et al. The emerging role of calmodulin regulation of RyR2 in controlling heart rhythm, the progression of heart failure and the antiarrhythmic action of dantrolene. Clinical and Experimental Pharmacology. 2017, 44, 135-142.
Maxwell J., et al. Dantrolene prevents arrhythmogenic Ca2+ release in heart failure. Am J Physiol Heart Circ Physiol, 2012, 302: H953-H963.
Okuda, S. et al. OP35-5: Dantrolene suppresses arrhythmogenesis by inhibition of aberrant Ca2+ release mediated by CaMKH and Ca2+ buffering in troponin T-related hypertrophic cardiomyopathy, Journal of Cardiac Failure, vol. 21, No. 10S, Oct. 2015.

(Continued)

*Primary Examiner* — Raymond J Henley, III
(74) *Attorney, Agent, or Firm* — Bereskin & Parr LLP; Carmela De Luca; Amy Dam

(57) ABSTRACT

The present disclosure relates to methods for the chronic treatment of dyssynchronous cardiac dysfunction (including non-arrhythmia cardiac dysfunction such as heart failure, cardiomyopathy, viral myocarditis, ischemia induced cardiomyopathy, ischemia, chemotherapy, pacing induced cardiomyopathy or ion channel mutation related dysfunction) and for the prevention or treatment of diseases or conditions associated with dyssynchronous cardiac dysfunction. The method comprises chronically administering to a patient an effective amount of dantrolene, or derivative or analogs thereof (such as azumolene).

20 Claims, 10 Drawing Sheets

(56) References Cited

OTHER PUBLICATIONS

Si D., et al. Essential role of ryanodine receptor 2 phosphorylation in the effect of azumolene on ventricular arrhythmia vulnerability in a rabbit heart model. J Cardiovasc Electrphysiol. Sep. 2018, 29, 1705-1715.
Si. D., et al. Resynchronizing calcium transients without hardware: Cardiac resynchronization with RYR2 Modulators. Heart Rhythm, May 2018, 15, S644.
Bokhari M. M., et al. Safety of chronic cardiac ryanodine receptor modulation: A 10-year experience. Clinical Electrophysiology. Nov. 2018, 4, 1480-1481.
Satoh M. et al. Effect of dantrolene sodium on clacium-overloaded heart. Jpn Circ J, 1997; 61; 855-863.
Wasserstrom, J. A., et al. Multiple defects in intracellular calcium cycling in whole failing rat heart. Circ Heart Fail. 2009; 2; 223-232.

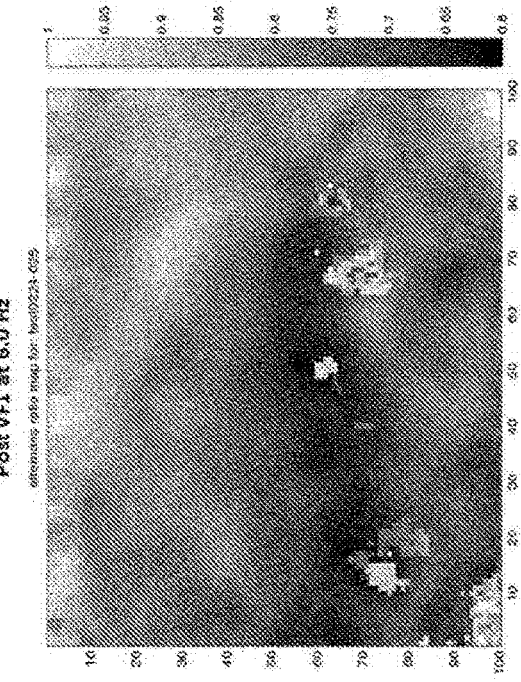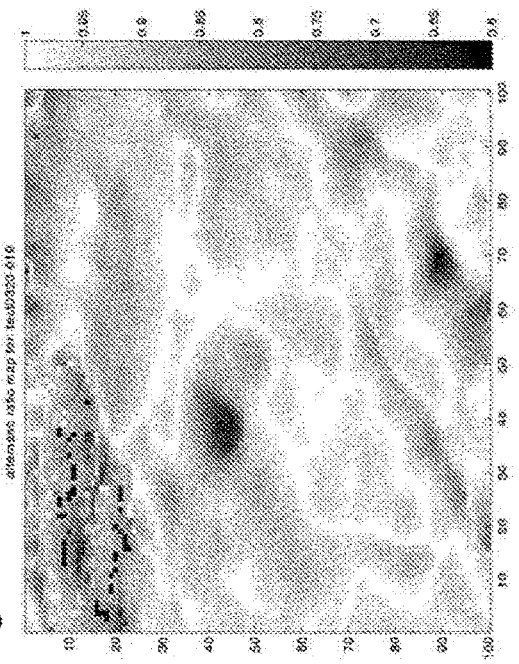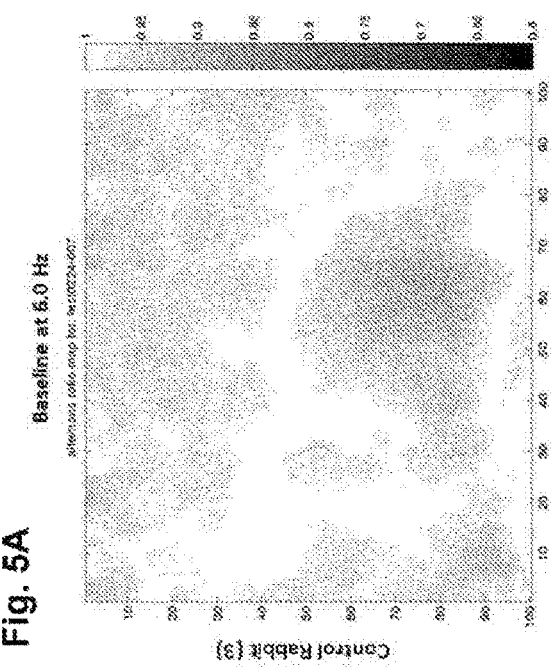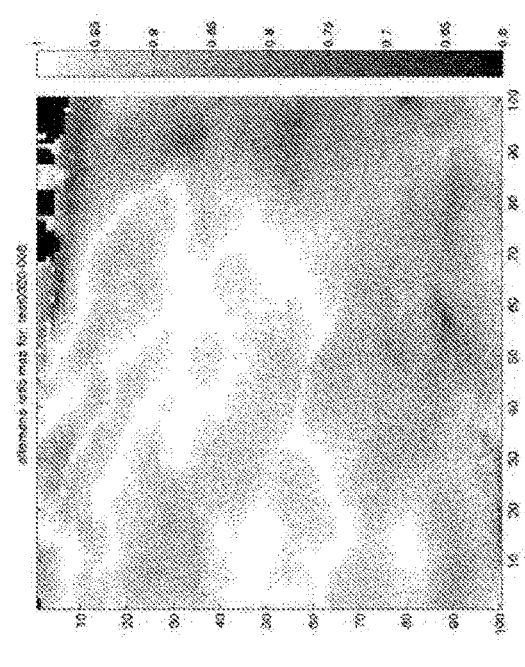

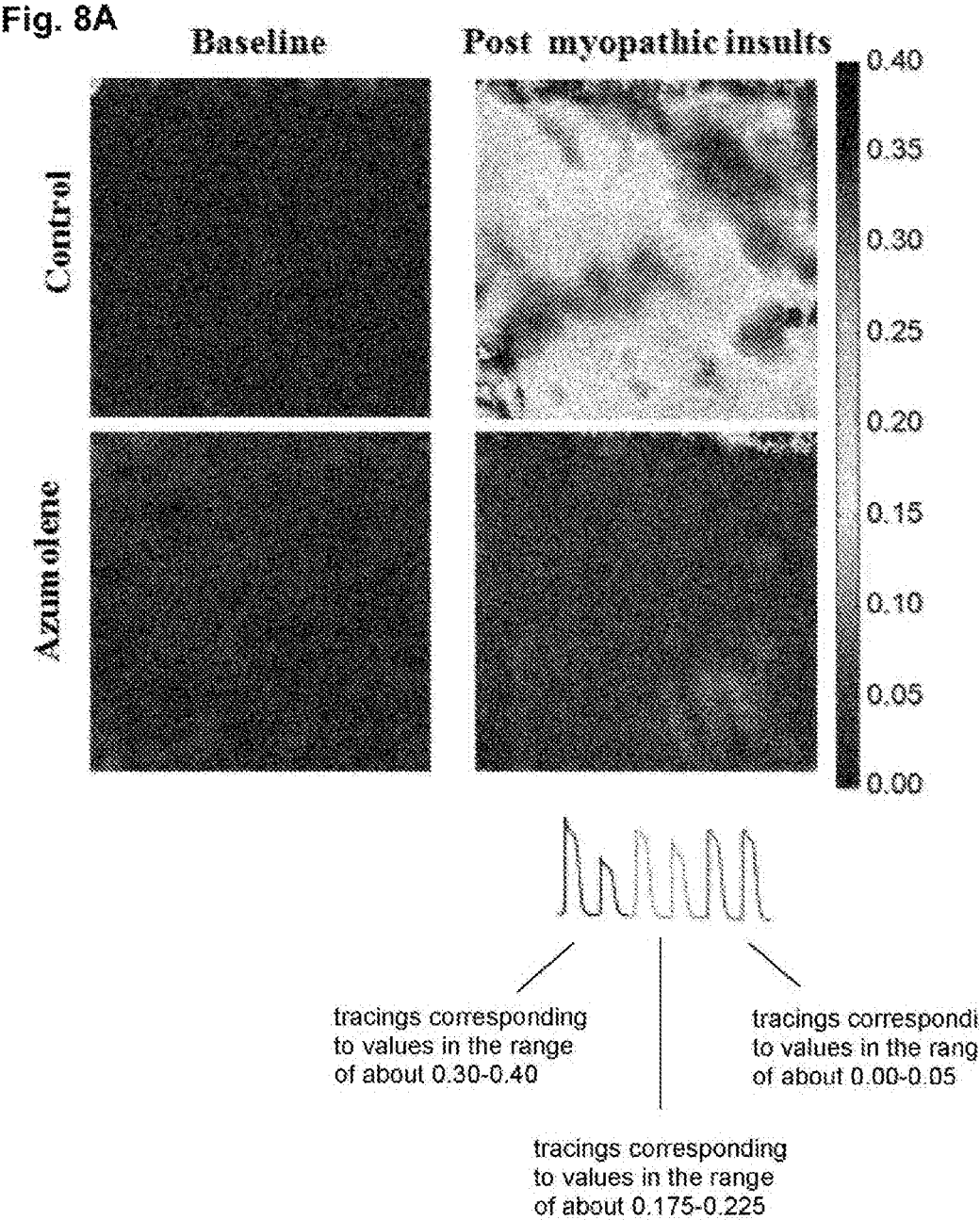

DANTROLENE AND ANALOGS THEREOF FOR THE CHRONIC TREATMENT AND PREVENTION OF DYSSYNCHRONOUS CARDIAC DYSFUNCTION

CROSS REFERENCE TO RELATED APPLICATIONS

This application is a national phase entry of PCT/CA2018/051443, filed Nov. 14, 2018, which claims the benefit of priority of U.S. Provisional Application Ser. No. 62/585,983 filed Nov. 14, 2017. All the teachings of the above-referenced applications are incorporated herein by reference.

FIELD OF THE DISCLOSURE

The present description relates to methods of treating or preventing dyssynchronous cardiac dysfunction and more particularly to methods of chronically treating and/or preventing dyssynchronous cardiac dysfunction, using dantrolene and/or analogs thereof.

BACKGROUND

Acute administration of dantrolene sodium in animal models immediately prior to inducing cardiac arrest was shown to be protective against cardiac arrhythmia [4]; however this finding was not useful in therapy, as the timing of a cardiac arrest is not generally predictable. U.S. Pat. No. 9,636,327, hereby incorporated by reference in its entirety, showed that acute administration of dantrolene following a cardiac arrest was effective for the acute treatment of cardiac arrhythmias.

While cardiac arrest is one potential cause of cardiac dysfunction, cardiac dysfunction and heart failure can also be caused by a variety of other situations. In general, treatments for individuals who have developed cardiac dysfunction are limited and are only moderately effective. The pharmacological treatments, exclusively target the deleterious neurohormonal activation and fibrosis, and do not address the dyssynchrony of the mechanical function. Of those that address mechanical dyssynchrony all of them involve hardware on or in the heart such as a cardiac resynchronizing pacemaker/defibrillator and a left ventricular assistive device (LVAD), that requires a cardiac device implantation, which is a significant surgical procedure and may cause complications.

Strategies for improving calcium cycling as a treatment, for example using sarco/endoplasmic reticulum $Ca^{2+}$-ATPase (SERCA), which is known to regulate calcium uptake into the cell, have been attempted [5]. However, a viral vector had to be used for this purpose and the primary dyssynchronous calcium release and uptake was not addressed. Attempts at better calcium release have been attempted with cardiac contractility modulation (CCRM) but could be only performed regionally with surgical procedure and with hardware on the heart.

A need remains for pharmacological therapeutic agents and methods effective for the treatment of dyssynchronous cardiac dysfunction, for the prevention of further worsening of dyssynchronous cardiac dysfunction, and/or for prevention of dyssynchronous cardiac dysfunction.

SUMMARY

The present disclosure relates to the use of dantrolene, or a derivative or analog thereof, for the chronic treatment of patients likely to develop dyssynchronous cardiac dysfunction, without regard to whether such patient has previously experienced a cardiac arrhythmia. It is demonstrated herein that dantrolene, or a derivative or analog thereof, may assist in the re-synchronizing of calcium cycling and may therefore prevent the development and/or worsening of dyssynchronous cardiac dysfunction.

Therefore, in one aspect there is provided a method for treatment or prevention of dyssynchronous cardiac dysfunction comprising chronically administering to a patient in need thereof a therapeutically effective amount of dantrolene, or a derivative, an analog, or a pharmaceutically acceptable salt of any of the foregoing or a mixture of any of the foregoing.

In an embodiment, the dyssynchronous cardiac dysfunction is a non-arrhythmia cardiac dysfunction.

In an embodiment, the dyssynchronous cardiac dysfunction is chemotherapy induced cardiomyopathy.

In an embodiment, the dantrolene pharmaceutically acceptable salt is dantrolene sodium.

In an embodiment, the dantrolene analog is azumolene or a pharmaceutically acceptable salt thereof.

The preceding section is provided by way of example only and is not intended to be limiting on the scope of the present disclosure and appended claims. Additional objects and advantages associated with the compositions and methods of the present disclosure will be appreciated by one of ordinary skill in the art in light of the instant claims, description, and examples. For example, the various aspects and embodiments of the disclosure may be utilized in numerous combinations, all of which are expressly contemplated by the present description. These additional advantages objects and embodiments are expressly included within the scope of the present disclosure. The publications and other materials used herein to illuminate the background of the disclosure, and in particular cases, to provide additional details respecting the practice, are incorporated by reference, and for convenience are listed in the appended reference.

BRIEF DESCRIPTION OF THE DRAWINGS

Further objects, features and advantages of the disclosure will become apparent from the following detailed description taken in conjunction with the accompanying figures showing illustrative embodiments of the disclosure, in which:

FIG. 2 is a series of calcium release tracings measured in disparate regions of rabbit myocardium and highlights the spatial dyssynchrony of calcium transients.

FIG. 5 is a series of calcium alternans ratio maps measured on rabbit hearts. FIG. 5A shows spatial distribution of calcium alternans in untreated rabbit heart at baseline (6.0 Hz). FIG. 5B shows spatial distribution of calcium alternans in untreated rabbit heart at post 1st VF at 6.0 Hz. FIG. 5C shows spatial distribution of calcium alternans in azumolene treated rabbit heart at baseline (6.0 Hz). FIG. 5D shows spatial distribution of calcium alternans in azumolene treated rabbit heart at post 1st VF at 6.0 Hz.

FIG. 8A is a series of calcium alternans ratio maps measured on azumolene-treated and untreated animal hearts at baseline and post myopathic insults. In the control heart at baseline measurement (top left image), the values range mostly from 0.00 to 0.025; in the azumolene-treated heart at baseline (bottom left image), the values range mostly from 0.025 to 0.05; in the control heart post myopathic insults (top right image), the values range mostly from 0.1 to 0.4 (the top right region showing ranges from 0.1 to 0.15 mostly and the bottom left region showing ranges from 0.15 to 0.4); and in the azumolene-treated heart post myopathic insults (bottom right image), the values range mostly from 0.05 to 0.1. The scale is from 0.00 to 0.40.

DETAILED DESCRIPTION OF THE DISCLOSURE

Figure 1B:
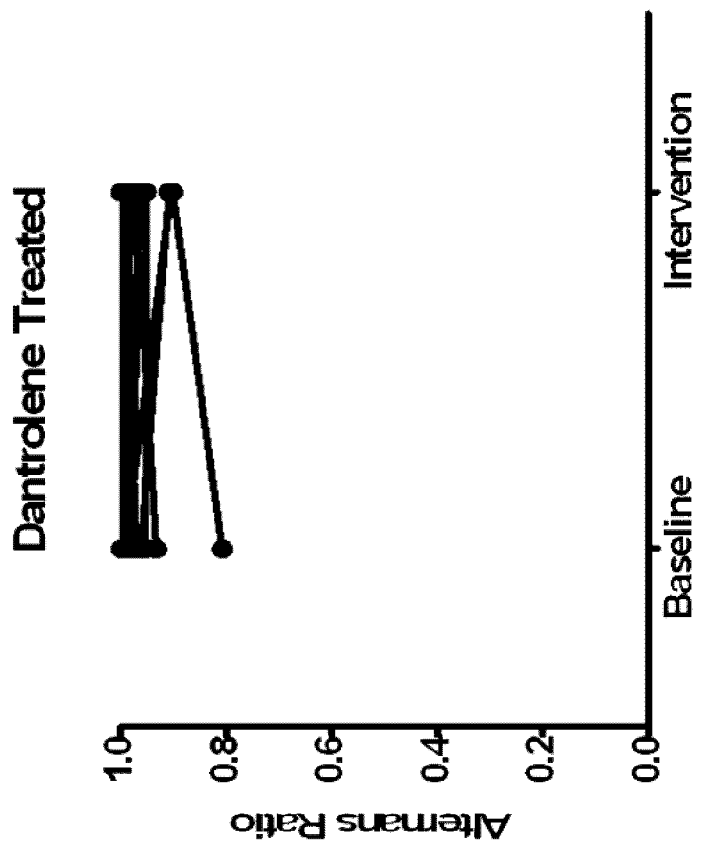
FIG. 1B is a graph showing that upon treating the rabbit hearts with dantrolene (sodium salt), the alternans ratio between at baseline and at intervention does not lower following heart fibrillation, at intervention. This suggests that pre-treatment with dantrolene may prevent the development of the spatio-temporal dyssynchrony.

The following is a detailed description provided to aid those skilled in the art in practicing the present disclosure.

Unless otherwise defined, all technical and scientific terms used herein have the same meaning as commonly understood by one of ordinary skill in the art to which this disclosure belongs. The terminology used in the description herein is for describing particular embodiments only and is not intended to be limiting of the disclosure. All publications, patent applications, patents, figures and other references mentioned herein are expressly incorporated by reference in their entirety.

I. DEFINITIONS

Unless defined otherwise, all technical and scientific terms used herein have the meaning commonly understood by a person skilled in the art to which this disclosure belongs. The appended references, the entire disclosures of which are incorporated herein by reference, provide one of skill with a general definition of many of the terms used in this disclosure.

As used herein, the following terms may have meanings ascribed to them below, unless specified otherwise. However, it should be understood that other meanings that are known or understood by those having ordinary skill in the art are also possible, and within the scope of the present disclosure. All publications, patent applications, patents, and other references mentioned herein are incorporated by reference in their entirety. In the case of conflict, the present specification, including definitions, will control. In addition, the materials, methods, and examples are illustrative only and not intended to be limiting.

The term "dyssynchronous cardiac dysfunction" as used herein means a cardiac dysfunction induced by, associated with or involving cardiac dyssynchrony and includes but is not limited to cardiomyopathy including chemotherapy induced cardiomyopathy, viral cardiopathy, ischemia induced cardiomyopathy (e.g. due to coronary artery disease), non-arrhythmia cardiac dysfunctions, heart failure, and ion channel mutation related dysfunction as well as chronic arrhythmia related dysfunctions such as heart failure. For example, the dyssynchronous cardiac dysfunction may be associated with calcium alternans ratios of 0.8 or less, 0.7 or less, 0.6 or less or 0.5 or less. As another example the dyssynchronous cardiac dysfunction may be associated with mean standard deviations in calcium alternans ratios of greater than 0.05, greater than 0.06 or greater than 0.07.

The term "cardiac dyssynchrony" as used herein means improper synchronization of calcium cycling in the heart or a part thereof, including for example temporal dyssynchrony and/or spatial dyssynchrony, optionally due to calcium leak from ryanodine type 2 receptor (RyR2) channels, leading to decreased calcium uptake and/or release in the sarcoplasmic reticulum (SR). RyR2 are found primarily in cardiac muscle and are a major mediator for SR release of calcium ions. Spatio-temporal dyssynchrony of calcium alternans can be measured by calculating a calcium alternans ratio (CaAR) for temporal mechanical dyssynchrony or by measuring the standard deviation (SD) of CaAR as a surrogate for spatial mechanical dyssynchrony. CaAR can be calculated as the amplitude of a Ca peak divided by the amplitude of a following Ca peak in a calcium transient measurement such as in FIG. 5. The smallest amplitude of Ca peak is divided by the largest amplitude of Ca peak. The larger the ratio the more similar the peak sizes. A ratio of 1 indicates no calcium alternans. Ratios of less than 1, optionally 0.8, 0.7 etc are indicative of cardiac dyssynchrony. Similarly mean standard deviations in calcium alternans ratios of greater than 0.05, greater than 0.06 or greater than 0.07 etc are indicative of cardiac dyssynchrony.

The term "dyssynchronous diastolic uptake and release dysfunction due to calcium leakage" as used herein means a type of dyssynchronous cardiac dysfunction.

The term "cardiac disease" includes "dyssynchronous cardiac dysfunctions" and cardiac conditions resulting therefrom, for example LBBB, intraventricuar conduction delay, wide qrs, RBBB.

The term "RyR2 modulator" means any compound or agent that binds ryanodine receptor 2 (also referred to as "RyR2", "RYR-2" or "RyR-2") and reduces calcium leak from ryanodine receptor type 2 (RyR2) channels. For example, the RyR2 modulator can be dantrolene, or a derivative, analog, pharmaceutically acceptable salt, solvate, hydrate or mixture thereof.

The term "dantrolene" as used herein means the compound having the structure:

and pharmaceutically acceptable salts thereof. Pharmaceutically acceptable salts thereof include dantrolene sodium salt, including the hydrated salt. Dantrolene can be produced according to methods known in the art, for example as described in U.S. Pat. No. 3,415,821, incorporated herein by reference in its entirety.

The term "azumolene" as used herein means the compound having the structure:

and pharmaceutically acceptable salts thereof.

Pharmaceutically acceptable salts thereof include azumolene sodium salt, including the hydrated salt. Azumolene can be produced according to methods known in the art, for example as described in U.S. Pat. No. 4,049,650, incorporated herein by reference in its entirety. Azumolene is an analog of dantrolene.

"Derivatives" as used herein means compounds formed from the native compounds either directly, by modification, or by partial substitution. For example, in certain embodiments, a derivative is a pharmaceutically acceptable prodrug form (such as an ester, amide other prodrug group) which, upon administration to a patient, provides directly or indirectly the present compound or an active metabolite of the present compound.

"Analogs" as used herein means compounds that have a structure similar to, but not identical to, the native compound. As mentioned above azumolene is an analog of dantrolene.

The term "pharmaceutically acceptable" as used herein means a salt, solvate or hydrate that is suitable for use with humans and/or animals without undue adverse side effects, such as toxicity, irritation, and allergic response or similar.

The term "pharmaceutically acceptable salt" as used herein means salts derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred. For example, a compound (e.g. dantrolene) can be presented in a pharmaceutically acceptable salt form (e.g. dantrolene sodium) to increase the solubility in the gastric juices of the patient's gastrointestinal tract in order to promote dissolution of the compound.

The term "mixture" as used herein means a composition comprising two or more compounds. In an embodiment a mixture is a mixture of two or more distinct compounds. In a further embodiment, when a compound is referred to as a "mixture", this means that it can comprise two or more "forms" of the compounds, such as, salts, solvates, prodrugs or, where applicable, stereoisomers of the compound in any ratio. A person of skill in the art would understand that a compound in a mixture can also exist as a mixture of forms. For example, a compound may exist as a hydrate of a salt.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives (including prodrug forms) thereof where applicable, in context. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity.

The term "prodrug" as used herein refers to a derivative of an active form of a known compound or composition which derivative, when administered to a patient, is gradually converted to the active form to produce a better therapeutic response and/or a reduced toxicity level. In general, prodrugs will be functional derivatives of the compounds disclosed herein which are readily convertible in vivo into the compound from which it is notionally derived. Prodrugs include, without limitation, acyl esters, carbonates, phosphates, and urethanes. These groups are exemplary and not exhaustive, and one skilled in the art could prepare other known varieties of prodrugs. Prodrugs may be, for example, formed with available hydroxy, thiol, amino or carboxyl groups. Some common esters which have been utilized as prodrugs are phenyl esters, aliphatic ($C_1$-$C_{24}$) esters, acyloxymethyl esters, carbamates and amino acid esters. Conventional procedures for the selection and preparation of suitable prodrugs are described, for example, in "Design of Prodrugs" ed. H. Bundgaard, Elsevier, 1985.

Where the compounds according to the disclosure possess one or more than one asymmetric centres, they may exist as "stereoisomers", such as enantiomers and diastereomers. It is to be understood that all such stereoisomers and mixtures thereof in any proportion are encompassed within the scope of the present disclosure. It is to be understood that, while the stereochemistry of the compounds of the disclosure may be as provided for in any given compound shown herein, such compounds may also contain certain amounts (e.g. less than 20%, less than 10%, less than 5%) of compounds having alternate stereochemistry.

The term "solvate" as used herein means a compound or its pharmaceutically acceptable salt, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates will vary depending on the compound and the solvate. In general, solvates are formed by dissolving the compound in the appropriate solvent and isolating the solvate by cooling or using an antisolvent. The solvate is typically dried or azeotroped under ambient conditions.

As used herein, "administered before onset of the dyssynchronous cardiac dysfunction" means that the dantrolene, or derivative, analog, or solvate or hydrate thereof or mixture of any of the foregoing is administered to the patient in need of cardio-protection, for example a patient who has or will be commencing chemotherapy treatment or other cardiotoxic treatment, or a patient that exhibits calcium cycling dyssynchrony but prior to detection, manifestation and/or diagnosis of the dyssynchronous cardiac dysfunction. It can also mean for example prior to the onset of a particular dyssynchronous cardiac dysfunction. Dantrolene and azumolene may have no effect on normally functioning RyR2, however binds dysfunctional RyR2, for example dysfunctional RyR2 causing calcium cycling dyssynchrony.

The terms "treat", "treating", and "treatment", etc., as used herein, refer to any action providing a benefit to a patient for which the present compounds may be administered. Benefits can include, but are not limited to, alleviation or amelioration of one or more symptoms or conditions, diminishment of extent of disease, stabilized (i.e. not worsening) state of disease, preventing spread or progression of disease, delay or slowing of disease progression, amelioration or palliation of the disease state, diminishment of the reoccurrence of disease. "Treat", "treating" and "treatment" can also mean prolonging survival as compared to expected survival if not receiving treatment. "Treat", "treating" and "treatment" as used herein also include prophylactic treatment. Treatment methods comprise administering to a patient a therapeutically effective amount of a compound described herein. For example, the compounds described herein may be administered at least once a week. However, in another embodiment, the compounds may be administered to the patient from about one time per three weeks, or about one time per week to about once daily for a given treatment. In one embodiment, the compound is administered once daily. In another embodiment, the compound is administered twice daily. In yet another embodiment, the compound is administered three times daily. In a further embodiment, the compound is administered four times daily. It will also be appreciated that the effective dosage of the compound used for the treatment or prophylaxis may increase or decrease over the course of a particular treatment or prophylaxis regime.

As used herein, "chronically administering" means administering to a patient in need thereof one or more compounds described herein in an amount and for a duration sufficient for treatment and/or prevention of dyssynchronous cardiac dysfunction, e.g. 400 mg/day of dantrolene sodium for at least six months, or 400 mg/day of dantrolene sodium for at least one year.

The term "patient in need thereof" as used herein means a patient at risk of cardiac dysfunction in need of cardioprotection, for example a patient who has or will be commencing chemotherapy treatment or other cardiotoxic treatment, or a patient that exhibits calcium cycling dyssynchrony but prior to onset of the dyssynchronous cardiac dysfunction (e.g. prior to detection, manifestation and/or diagnosis of the dyssynchronous cardiac dysfunction).

The term "coadministration" or "combination therapy" shall mean that at least two compounds or compositions are administered to the patient at the same time, such that effective amounts or concentrations of each of the two or more compounds may be found in the patient at a given point in time. Although compounds according to the present disclosure may be co-administered to a patient at the same time, the term embraces both administration of two or more agents at the same time or at different times, provided that effective concentrations of all coadministered compounds or compositions are found in the patient at a given time.

The term "effective amount" or "therapeutically effective amount" means an amount effective, at dosages and for periods of time necessary to achieve the desired result. For example in the context or treating or preventing a dyssynchronous cardiac dysfunction, an effective amount is an amount that, for example, causes resynchronization of calcium cycling in the myocardium compared to untreated myocardium. Effective amounts may vary according to factors such as the disease state, age, sex, weight of the patient. The amount of a given compound that will correspond to such an amount will vary depending upon various factors, such as the given drug or compound, the pharmaceutical formulation, the route of administration, the type of dyssynchronous cardiac dysfunction, the patient being treated, and the like.

The term "administered" as used herein means administration of a therapeutically effective dose of a compound or composition of the disclosure to a cell either in cell culture or in a patient.

The term "dosage form" as used herein refers to the physical form of a dose for example comprising a compound of the disclosure, and includes without limitation injectable dosage forms, including, for example, sterile solutions and sterile powders for reconstitution, and the like, that are suitably formulated for injection, liquid and solid dosage forms including, for example tablets, including enteric coated tablets, caplets, gelcaps, capsules, ingestible tablets, buccal tablets, troches, elixirs, suspensions, syrups, wafers, resuspendable powders, liquids and solutions. For example the injectable dosage form can be a subcutaneous, intradermal, or intramuscular depot injection that allows the compound to be released in a controlled and consistent way over a period of time, for example over one month. Methods for making depot injections are described, for example, in U.S. Pat. No. 3,089,815 entitled "Injectable pharmaceutical preparation, and a method of making same" and herein incorporated by reference in its entirety.

The term "patient" as used herein refers to an animal, preferably a human or a domesticated animal, to whom treatment, including prophylactic treatment, with the compositions according to the present disclosure is provided. For treatment of those conditions or disease states which are specific for a specific animal such as a human patient, the term patient refers to that specific animal. In general, in the present disclosure, the term patient refers to a human patient unless otherwise stated or implied from the context of the use of the term.

Where a range of values is provided, it is understood that each intervening value, to the tenth of the unit of the lower limit unless the context clearly dictates otherwise, between the upper and lower limit of that range and any other stated or intervening value in that stated range is encompassed within the description. Ranges from any lower limit to any upper limit are contemplated. The upper and lower limits of these smaller ranges which may independently be included in the smaller ranges is also encompassed within the description, subject to any specifically excluded limit in the stated range. Where the stated range includes one or both of the limits, ranges excluding either both of those included limits are also included in the description.

Although any methods and materials similar or equivalent to those described herein can also be used in the practice or testing of the present disclosure, the preferred methods and materials are now described.

It must be noted that as used herein and in the appended claims, the singular forms "a", "an", and "the" include plural references unless the context clearly dictates otherwise.

All numerical values within the detailed description and the claims herein are modified by "about" or "approximately" the indicated value, and take into account experimental error and variations that would be expected by a person having ordinary skill in the art.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" or, when used in the claims, "consisting of" will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

The term "about" as used herein means plus or minus 0.1 to 50%, 5-50%, or 10-40%, 10-20%, 10%-15%, preferably 5-10%, most preferably about 5% of the number to which reference is being made It should also be understood that, in certain methods described herein that include more than one step or act, the order of the steps or acts of the method is not necessarily limited to the order in which the steps or acts of the method are recited unless the context indicates otherwise.

II. METHODS

It is hypothesized that cardiomyopathy from a variety of causes such as ischemia, viral myocarditis, chemotherapy and pacing induced dysfunction may be partly due to reduced rates of calcium cycling and dyssynchronous calcium cycling. A main defect in this electrical-contraction coupling is that the Ryanodine Receptor 2 (RyR2) is leaky and dyssynchronous in the failing myocardium which translates to cellular contractile dysfunction. It has been shown that loss of T-tubular RyR2 dislocation causes anatomic and functional dissociation which leads to electrical activation that is disconnected from the calcium cycling in myocardial regions. This leads to one myocyte contracting against another myocyte that is not fully engaged by the calcium machinery, resulting in a significant reduction in contractility. The disordered calcium release exhibits a highly fractionated calcium cellular wave front, resulting in a pattern of mechanical dyssynchrony.

Reduced rates of calcium cycling are likely to contribute to diminished contractile performance. Loss of cardiac transverse tubules (t-tubules) leads to anatomic and functional dissociation between electrical activation and release of $Ca^{2+}$ from the sarcoplasmic reticulum (SR); there is less $Ca^{2+}$ accessing the L-type calcium channel, and the ensuing delay in activation of RyR2 results in poorly coordinated release of $Ca^{2+}$ during contractility and a highly fractionated cellular wavefront among myocytes. Furthermore, if one myocyte tugs on its neighbor before the neighbor has been activated, this has the effect of significantly reducing contractility. Spatial and temporal $Ca^{2+}$ alternans has been reported.

Unexpectedly, it has been found that resynchronizing calcium cycling in cardiac tissue that had been made dyssynchronous leads to better contractile function. It is also demonstrated herein that resynchronization of calcium cycling may be achieved using a non-device based strategy of resynchronizing physiology, by administering a RyR2 modulator. The experiments described herein suggest that administration of RyR2 modulators may prevent development and progression of cardiac dysfunction related to calcium desynchronization.

Dantrolene sodium (1-[[5-(p-nitrophenyl)furfurylidene]-amino]hydantoin sodium salt) is described in U.S. Pat. No. 3,415,821, incorporated herein by reference in its entirety. Historically, dantrolene sodium has been used as a skeletal muscle relaxant particularly in controlling the manifestations of clinical spasticity resulting from upper neuron disorders. (Physicians' Desk Reference, 36th Edition, 1982). Formulations comprising therapeutically effective amounts of dantrolene sodium are known to those of skill in the art as described for example in U.S. Patent Publication 2009/0093531, which is incorporated herein by reference in its entirety.

Dantrolene and azumolene were found to exhibit preventative effects. As shown in Example 1, treatment of failing hearts with a RyR2 modulator, e.g. dantrolene or azumolene administered prior to myopathic stress, was found to minimize heterogeneity in calcium alternans in response to the myopathic stress as well as resynchronize calcium cycling, thus improving cardiac resynchronization.

Accordingly provided herein in one aspect, is a method for resynchronizing cardiac calcium levels in a patient, the method comprising chronically administering to a patient in need thereof a therapeutically effective amount of dantrolene, or a derivative, an analog, solvate or hydrate thereof or a mixture of any of the foregoing.

Resynchronizing dysnchronous calcium transients can be important for early treatment of dyssynchronous cardiac dysfunctions, preventing for example more serious manifestations.

Thus, in another aspect, there is provided a method for treating or preventing dyssynchronous cardiac dysfunction comprising chronically administering to a patient in need thereof a therapeutically effective amount of dantrolene, or a derivative, an analog, a solvate or hydrate or a mixture of any of the foregoing.

In an embodiment, the treatment is for slowing or inhibiting progression of an existing dyssynchronous cardiac dysfunction.

In an embodiment, the method is for preventing progression to a more serious dyssynchronous cardiac dysfunction or cardiac disease.

In an embodiment, the dyssynchronous cardiac dysfunction is due to ischemic or idiopathic causes that affect calcium cycling. For example, the method disclosed herein is effective for altering calcium dyssynchrony.

In an embodiment, the patient is in need due to risk of dyssynchronous cardiac dysfunction and the dantrolene, or derivative, analog, solvate or hydrate thereof or mixture of the foregoing is administered before onset of the dyssynchronous cardiac dysfunction.

In an embodiment, the patient in need thereof is exempt of cardiac arrest and/or has not had a cardiac arrest.

For example, the patient may be starting a drug treatment that is cardiotoxic and/or associated with cardiomyopathy, such as chemotherapy. In such situations, the dantrolene or derivative, analog, solvate or hydrate thereof or mixture of the foregoing can be administered before the drug treatment or during the drug treatment and before onset e.g. before detection, manifestation and/or diagnosis of dyssynchronous cardiac dysfunction.

In an embodiment, the patient is in need due to risk of cardiac dysfunction and the dantrolene, derivative, analog, or solvate or hydrate thereof or mixture of any of the foregoing is administered before and after onset of the dyssynchronous cardiac dysfunction or cardiac disease.

In an embodiment, the patient is in need due to a history of dyssynchronous cardiac dysfunction or cardiac disease. For example, the patient has dyssynchronous cardiac dysfunction or cardiac disease due to repeated chemotherapy (e.g. chemotherapy induced cardiomyopathy), diastolic, or ischemic heart failure states.

In an embodiment, the dyssynchronous cardiac dysfunction is selected from chemotherapy induced cardiomyopathy, diastolic heart failure, ischemic heart failure and a non-arrhythmia cardiac dysfunction.

In one embodiment, the dyssynchronous cardiac dysfunction is a non-arrhythmia cardiac dysfunction.

For example, the non-arrhythmia dyssynchronous cardiac dysfunction is selected from heart failure, cardiomyopathy including viral myocarditis and ischemia, chemotherapy or pacing induced cardiomyopathy, and ion channel mutations that lead to dyssynchronous calcium leaks.

Hanna et al [6] have demonstrated that the anthracycline cardiotoxicity is due to its direct action on RyR2 channels and impaired cardiac Ca2+ handling. Anthracyclines and potentially other chemotherapeutic agents may thus disrupt Ca2+ handling and produce calcium dyssynchrony, and impair cardiac function by directly targeting RyR2 function.

In one embodiment, the dyssynchronous cardiac dysfunction is chemotherapy induced cardiomyopathy.

A further aspect provides a method of reducing drug induced cardiomyopathy, the method comprising, administering an effective amount of dantrolene, a derivative, an analog, or solvate or hydrate thereof or mixture of any of the foregoing to a patient undergoing or commencing a cardiotoxic treatment.

In one embodiment, the dyssynchronous cardiac dysfunction is viral myocarditis or viral cardiomyopathy.

In one embodiment, the dyssynchronous cardiac dysfunction is associated with and/or induced by calcium alternans.

In an embodiment, the dyssynchronous cardiac dysfunction is pacing induced cardiomyopathy.

In an embodiment, the patient has no history of cardiac dysfunction.

In an embodiment, the dantrolene, derivative, analog, or solvate or hydrate thereof or mixture of any of the foregoing is administered during or immediately following detection of the dyssynchronous cardiac dysfunction.

In an embodiment, the treatment obviates the need for installation of a left ventricular assistive device or a cardiac contractility modulation (CCM) device.

In another aspect, there is provided a method for treatment of dyssynchronous diastolic uptake and release dysfunction due to calcium leakage wherein spatial discordance and/or calcium transients are resynchronized, optionally in elderly patients at risk of or experiencing dyssynchronous diastolic uptake and release dysfunction, comprising administering to a patient in need thereof a therapeutically effective amount of dantrolene, or a derivative, an analog, solvate or hydrate thereof or a mixture of any of the foregoing.

In one embodiment, the methods comprise co-administering an effective amount of at least one additional agent prior, contemporaneously, or subsequent to administration of the therapeutically effective amount of dantrolene, derivative, analog, solvate or hydrate or mixture thereof, e.g., dantrolene sodium, azumolene or combination thereof, wherein the combination is effective in treating or preventing cardiac dysfunction and the detrimental effects that result therefrom.

In one embodiment, the dantrolene is the pharmaceutically acceptable salt.

In one embodiment, the azumolene is the pharmaceutically acceptable salt.

In any of the aspects or embodiments described herein, the dantrolene, dantrolene derivative or analog, solvate or hydrate or a mixture thereof comprises dantrolene sodium, azumolene or a mixture of both.

In one embodiment, the dantrolene, derivative, analog, solvate or hydrate or mixture of any of the foregoing comprises dantrolene sodium.

In one embodiment, the dantrolene analog is azumolene or solvate or hydrate thereof.

In an embodiment, the patient is a mammal. In still another embodiment, the patient is a human.

In an embodiment, the therapeutically effective amount of dantrolene, a dantrolene derivative or analog, or solvate or hydrate thereof or mixture of the foregoing is administered in one or more doses per day or per week. Furthermore, in any of the aspects or embodiments described herein, the therapeutically effective amount of dantrolene, a dantrolene derivative or analog, a solvate or hydrate or a mixture thereof is administered in a suitable pharmaceutically acceptable composition.

In an embodiment, the pharmaceutical composition is in a dosage form selected from a solid dosage form and a liquid dosage form.

In an embodiment, the pharmaceutical composition is administered by parenteral, intravenous, subcutaneous, intracardial, intramuscular, or oral administration.

In an embodiment, the pharmaceutical composition is in a dosage form selected from a solid dosage form and a liquid dosage form.

In an embodiment, the pharmaceutical composition is an injectable dosage form.

In an embodiment, the injectable liquid is an injectable liquid depot suitable, for example suitable for subcutaneous administration.

The dosage form administered can contain for example 5 mg, 10 mg, 20 mg, 25 mg, 50 mg or 100 mg of dantrolene, derivative, analog, or solvate or hydrate thereof or mixture of any of the foregoing per unit dosage. The daily dose can for example range from between 5 mg per day to 800 mg/day.

In one embodiment, the therapeutically effective of dantrolene derivative, analog, solvate or hydrate thereof or mixture of any of the foregoing is 25 mg/day, 50 mg/day, 75 mg/day, 100 mg/day, 125 mg/day, 150 mg/day, 175 mg/day, 200 mg/day, 225 mg/day, 250 mg/day, 275 mg/day, 300 mg/day, 325 mg/day, 350 mg/day, 375 mg/day, 400 mg/day, 425 mg/day, 450 mg/day, 475 mg/day or 500 mg/day.

In one embodiment, the therapeutically effective of dantrolene derivative, analog, solvate or hydrate thereof or mixture of any of the foregoing is 100 mg/day.

In one embodiment, the therapeutically effective amount of dantrolene derivative, analog, solvate or hydrate thereof or mixture of any of the foregoing is in the range of from about 0.1 µg/kg/day to about 1000 mg/kg/day.

In one embodiment, the therapeutically effective amount of dantrolene derivative, analog, solvate or hydrate thereof or mixture of any of the foregoing is about 2.5 mg/kg/day, about 5 mg/kg/day, about 10 mg/kg/day, about 15 mg/kg/day, about 20 mg/kg/day, about 25 mg/kg/day, about 30 mg/kg/day, about 35 mg/kg/day, about 40 mg/kg/day, about 45 mg/kg/day or about 50 mg/kg/day.

The compounds are chronically administered, for example typically over a period of at least 1 week or at least 6 months. For example, the compounds are administered once a day, twice a day or three times a day, for a period of at least 1 week or at least 6 months.

In an embodiment, the treatment is chronically administered for at least 3 months, at least 6 months, at least 1 year, at least 2 years, at least 3 years, at least 5 years, at least 10 years or longer. For example, the treatment can be a daily dose taken for a 3 months etc or until no longer needed, or can be a weekly dose taken for example for at least 3 months or 6 months etc for example until no longer needed.

Moreover, in any of the embodiments of uses or methods described herein, performance of the use or method can further effectuate at least one of an improvement in calcium temporal dyssynchrony, calcium spatial dyssynchrony, an improvement in hemodynamic performance, sustained return of spontaneous circulation (ROSC), reduction of time to ROSC, improved systolic blood pressure, improved diastolic blood pressure, improved diastolic function, improved cardiac contractility, reduction in calcium amplitude alternans (CaA-ALT), reduction in RyR2 hyperphosphorylation, reduction in RyR2 calcium leak, increased resistance to VF induction, improved survival or a combination thereof.

The formulations can be administered orally, topically, parenterally, by inhalation or spray, e.g., via dantrolene aerosol, or rectally in dosage unit formulations containing conventional non-toxic pharmaceutically acceptable carriers, adjuvants and vehicles. The term "parenteral" as used herein includes percutaneous, subcutaneous, intravascular (e.g., intravenous), intramuscular, or intrathecal injection or infusion techniques and the like. In addition, there is provided a pharmaceutical formulation comprising a dantrolene, derivative, analog, solvate or hydrate thereof or a mixture of any of the foregoing and a pharmaceutically acceptable carrier. One or more molecules of the disclosure can be present in association with one or more non-toxic pharmaceutically acceptable carriers and/or diluents and/or adjuvants, and if desired other active ingredients. The pharmaceutical compositions of the disclosure can be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present. Pharmaceutical compositions of the disclosure can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811, herein incorporated by reference in its entirety.

It is especially advantageous to formulate oral or parenteral compositions in dosage unit form for ease of administration and uniformity of dosage. Dosage unit form as used herein refers to physically discrete units suited as unitary dosages for the patient to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals.

III. EXAMPLES

Example 1: Resynchronizing Calcium Transients in Failing Hearts with RyR2 Modulators Background: Calcium handling in failing hearts has been shown to be dyssynchronous. Ryanodine receptor subtype 2 (RYR-2) expression has been documented to be more heterogeneous in dyssynchronous heart failure (DSH) compared to those with heart failure (HF) but without dyssynchrony [1]. This heterogeneity partially resolved after cardiac resynchronization therapy (CRT) in the same model [1]. The clinical benefit seen after CRT in DHF is likely due to correction of calcium handling [2]. Dantrolene has been shown to modulate RYR2 and correct calcium handling [3], [4].

Objective: To investigate the potential effect of RyR2 modulation as an agent to resynchronization of dyssynchronous calcium transients.

Methods: Two RYR-2 modulating agents were studied (azumolene (n=8) and dantrolene (n=7)) in two separate experiments. Their effect on temporal calcium alternans ratio (CaAR) before and after ventricular fibrillation (VF) (as a surrogate for temporal mechanical dyssynchrony) and standard deviation (SD) of CaAR from the anterior wall of left ventricular, which is used as a surrogate for spatial mechanical dyssynchrony, were assessed. In both experiments, twice VF (4 minutes) was induced electrically in Langendorff-perfused rabbit hearts, followed by azumolene (A) (20 μM), or dantrolene (D) (20 μmol/L) infusion in a randomized fashion (normal saline being the placebo arm). Simultaneous optical mapping was performed. Calcium alternans are defined as beat-to-beat variability of 10% or more in calcium transient amplitudes.

Figure 1A:
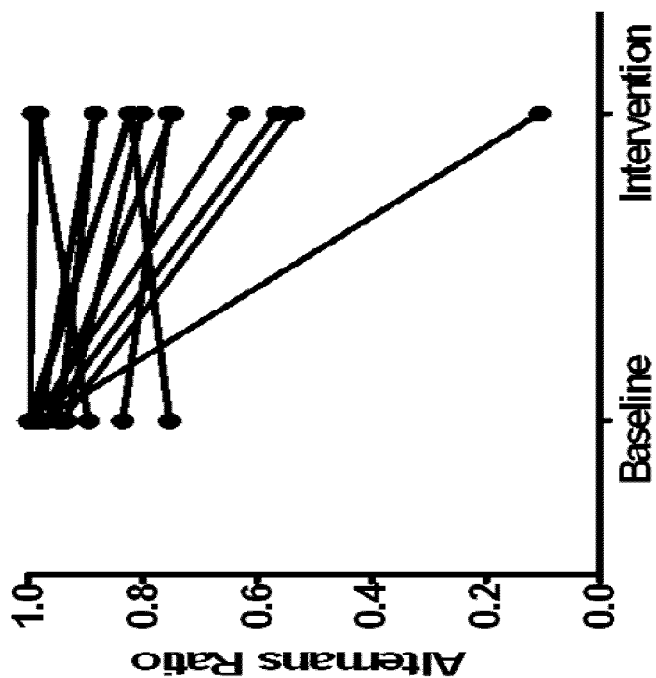
FIG. 1A is a graph showing the alternans ratio as a surrogate for temporal dyssynchrony of myopathic state measured in untreated rabbit hearts at baseline following which the hearts were fibrillated to produce that dyssynchronous state at intervention. The hearts in FIG. 1A received saline injections prior to producing heart failure state. A decreased alternans ratio between at baseline and at intervention suggests greater calcium temporal dyssynchrony.
Figure 4B:
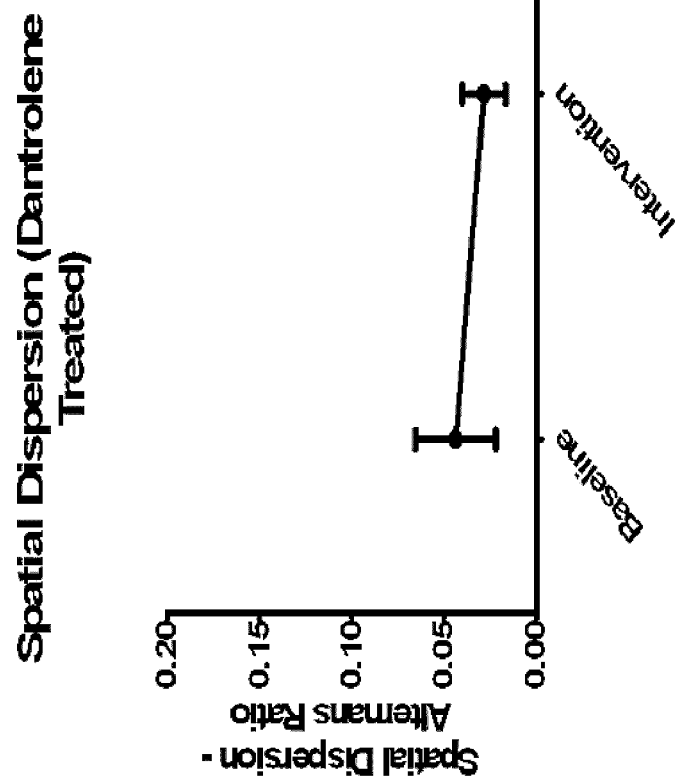
FIG. 4 is a series of graphs showing the standard error of the calcium alternans ratio, a surrogate of spatial disordering, measured in control hearts (untreated at baseline and saline-treated at intervention) (4A) and dantrolene-treated hearts (untreated at baseline and dantrolene-treated at intervention) (4B).
Figure 4A:
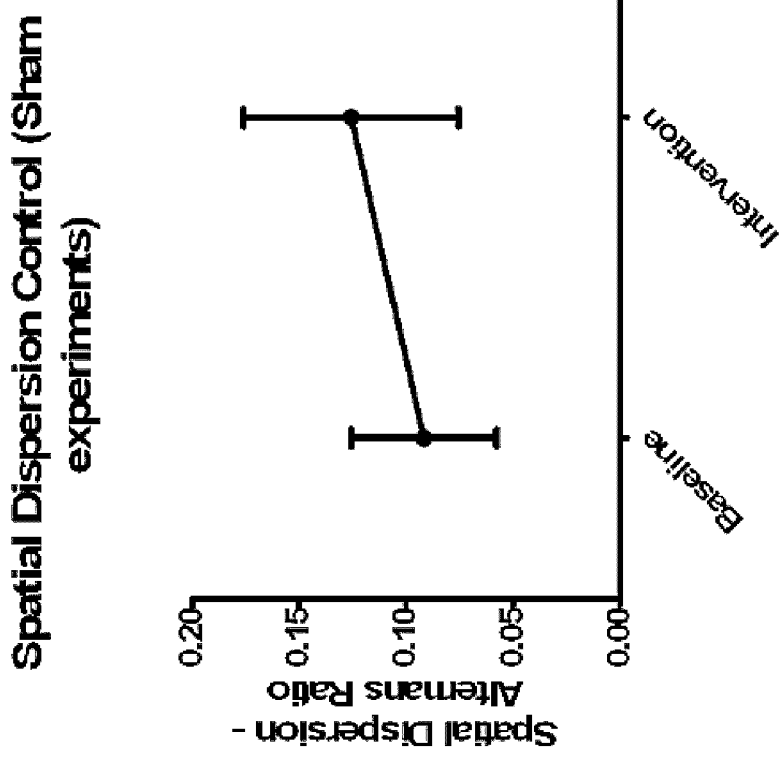

Results: The experiments were conducted to study calcium dyssynchrony in rabbit hearts and the therapeutic effect of RyR2 modulators dantrolene and azumolene in improving myocardial dysfunction. VF was used as a stress on the heart which produced a myopathic state similar to heart failure. As shown in FIGS. 1A and 1B, the calcium alternans ratios measured in saline-treated (FIG. 1A) and dantrolene-treated (FIG. 1B) hearts suggests that pre-treatment with dantrolene prevents development of temporal dyssynchrony. In FIG. 4, dantrolene-treated hearts (4B) also exhibited less spatial dispersion, as measured by the standard error of calcium alternans ratios, compared to control (saline-treated) hearts (4A).

Figure 2A:
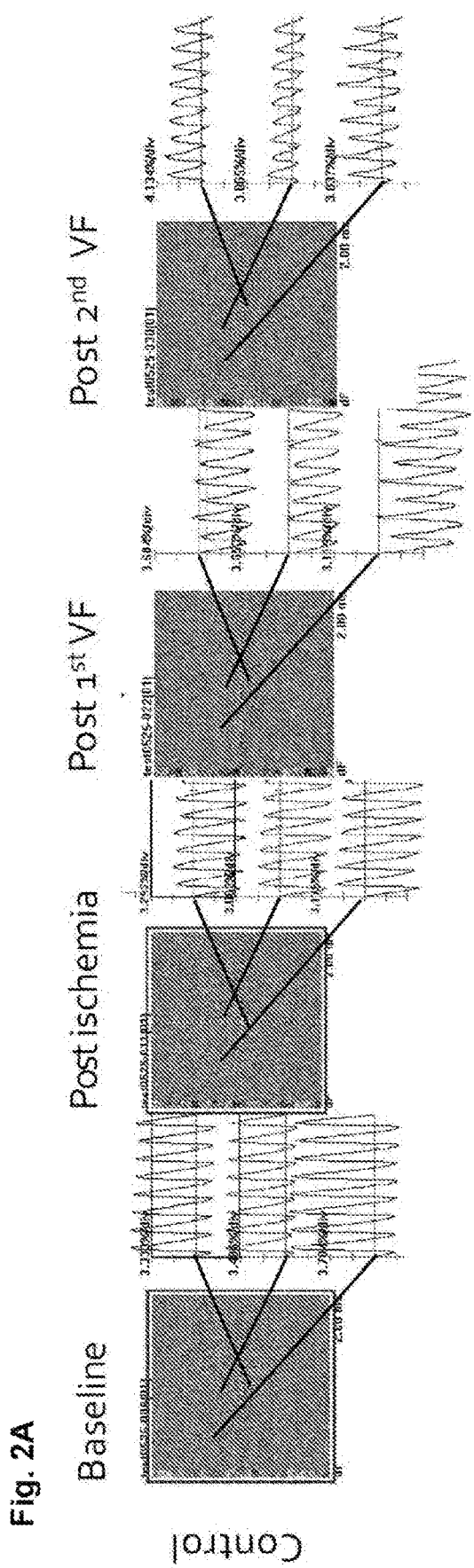
FIG. 2A is a series of calcium release tracings in control hearts and shows that after the stress of a ventricular fibrillation (VF) event, which makes the heart myopathic, spatial calcium dyssynchrony is manifested due to decreased and disordered spatial release.
Figure 2B:
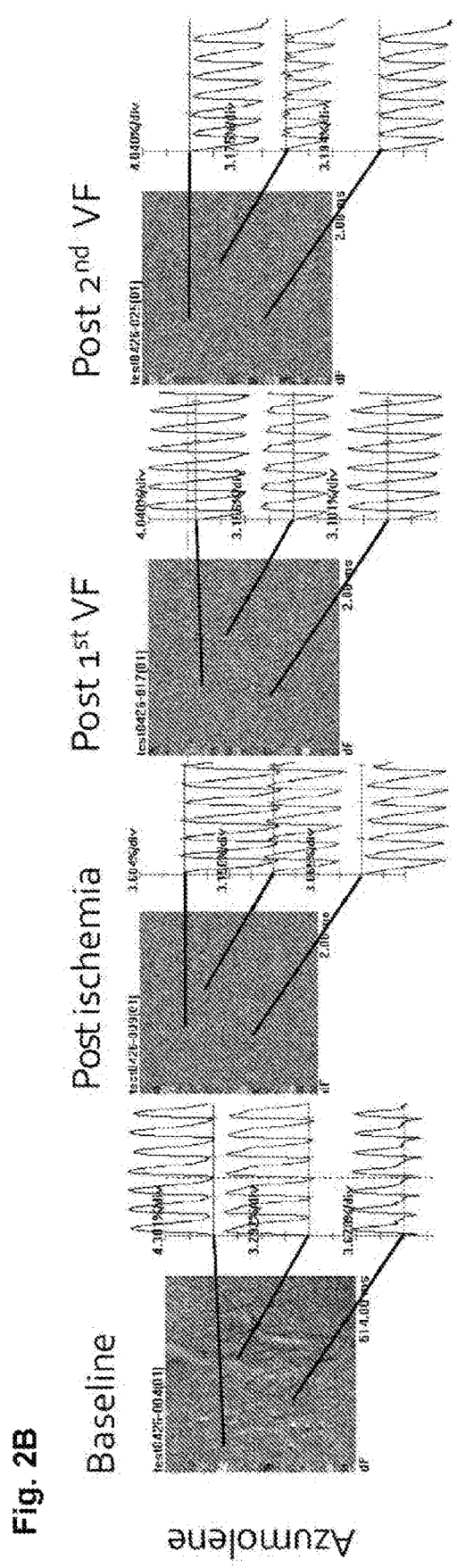
FIG. 2B is a series of calcium release tracings in azumolene treated hearts showing that in the presence of azumolene, spatial calcium release disordering is abrogated, suggesting that this dantrolene analog may prevent and treat spatial calcium dyssynchrony.
Figure 3:
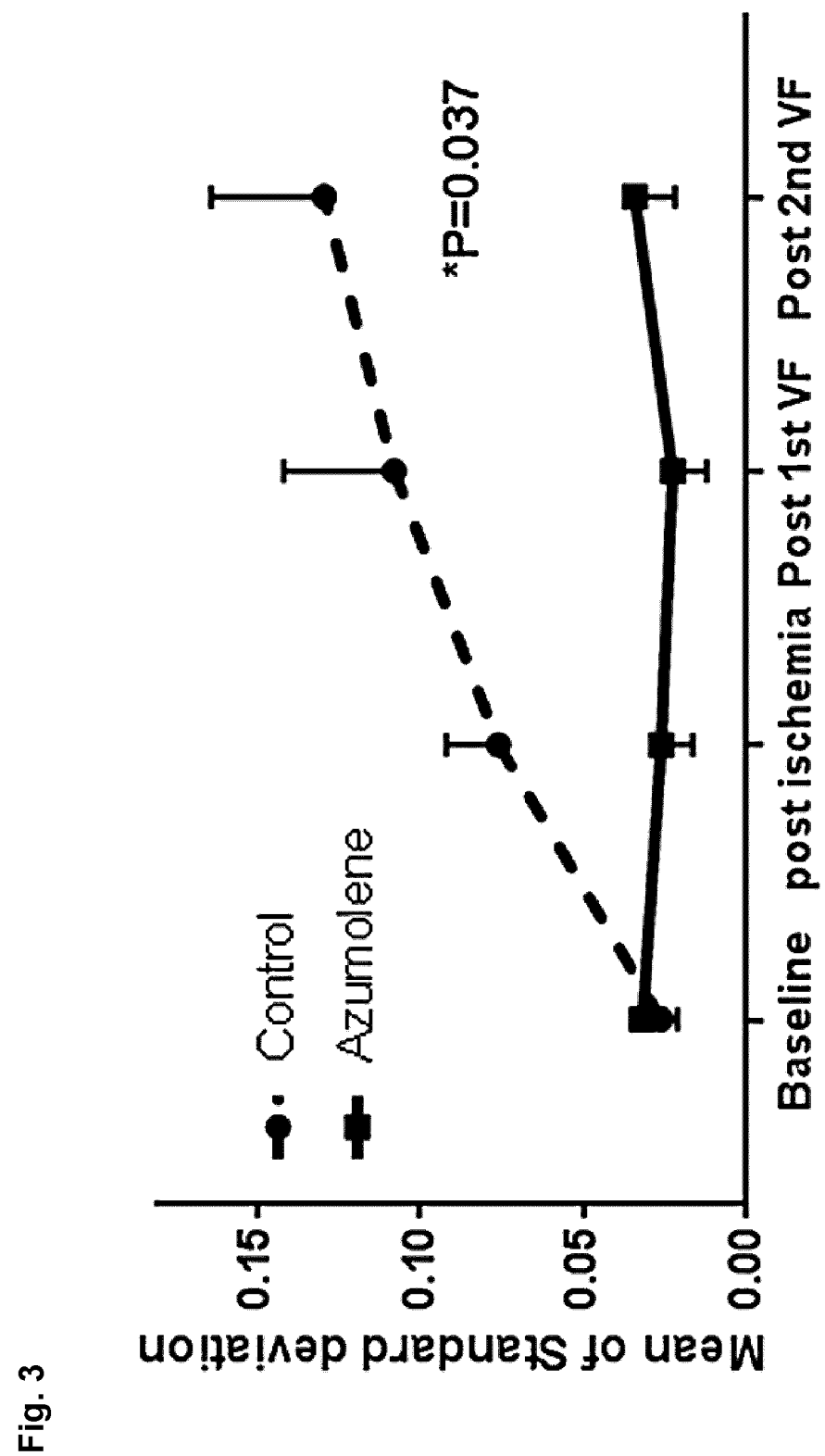
FIG. 3 is a graph showing the mean of standard deviation (SD) of calcium alternans at baseline, post-ischemia, post $1^{st}$ VF and post $2^{nd}$ VF between control (n=8) and azumolene-pretreated groups (n=8) at 200 ms cycle length (CL). After VF episodes, the SD significantly increased in the control group compared to the azumolene-pretreated group (*P=0.037, two way repeated measured ANOVA).

FIGS. 2 and 3 show the occurrence of spatial dyssynchrony in untreated compared to azumolene-treated rabbit hearts. As shown in FIG. 2B, treatment with azumolene reduced spacial calcium release dyssynchrony compared to untreated hearts (FIG. 2A). Similarly, as shown in FIG. 3, after VF episodes, the standard deviation significantly increased in the control group compared to the azumolene-treated group. The SD of CaAR was significantly increased in controls, compared to azumolene treated hearts, both after 1st VF (0.056±0.007 vs. 0.025±0.003, P=0.04) and 2nd VF (0.075±0.010 vs. 0.039±0.004, P=0.01). In the presence of azumolene, the standard deviation, used as a surrogate for spatial dyssynchrony, did not increase with repetitive myopathic stress induced on the heart. FIG. 5 is a series of calcium alternans ratio maps in untreated hearts and azumolene-treated hearts, measured at baseline and after the first VF. It can be seen that azumolene-treated hearts had fewer calcium alternans (5D) than untreated hearts (5B). CaAR was significantly decreased in control, compared to azumolene treated heart, after 1st VF (0.91±0.03 vs. 0.97±0.02, P<0.01) and 2nd VF (0.88±0.04 vs. 0.94±0.02, P<0.01).

RyR2 and calcium modulation with either dantrolene or azumolene minimizes heterogenity in calcium alternans in response to myopathic stress.

Example 2

Cardiac disease is known to be associated with certain chemotherapy drugs. The severity of symptoms depends on the type of chemotherapy drug received and on the patient's history. Symptoms may occur during chemotherapy or months after the chemotherapy ended and damages to the heart may be permanent. Dantrolene or azumolene will be tested in a mouse model for a human cancer. The compound will be administered to the mice prior to chemotherapy and its safety and effectiveness will be assessed. It will be determined whether chemotherapy drugs may play a role in mediating RyR2 receptors and whether dantrolene/azumolene are effective in reducing calcium cycling dyssynchrony.

Example 3

Figure 6A:
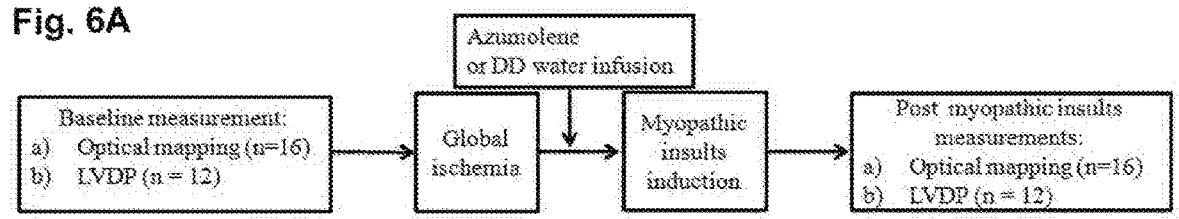
FIGS. 6A and 6B are a schematic and images, respectively, of the experimental protocol of animal hearts, pretreated or not with azumolene, subjected to myopathic insults.
Figure 6B:
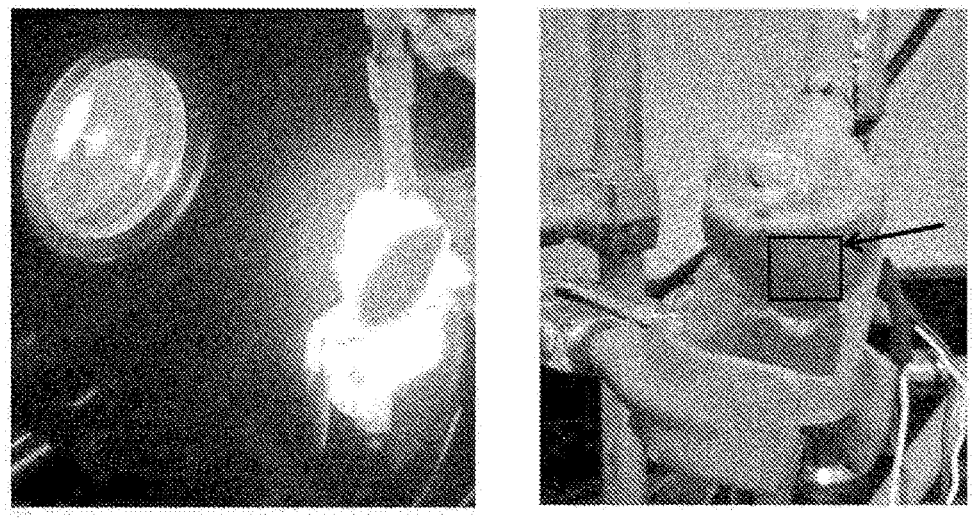
Figure 7A:
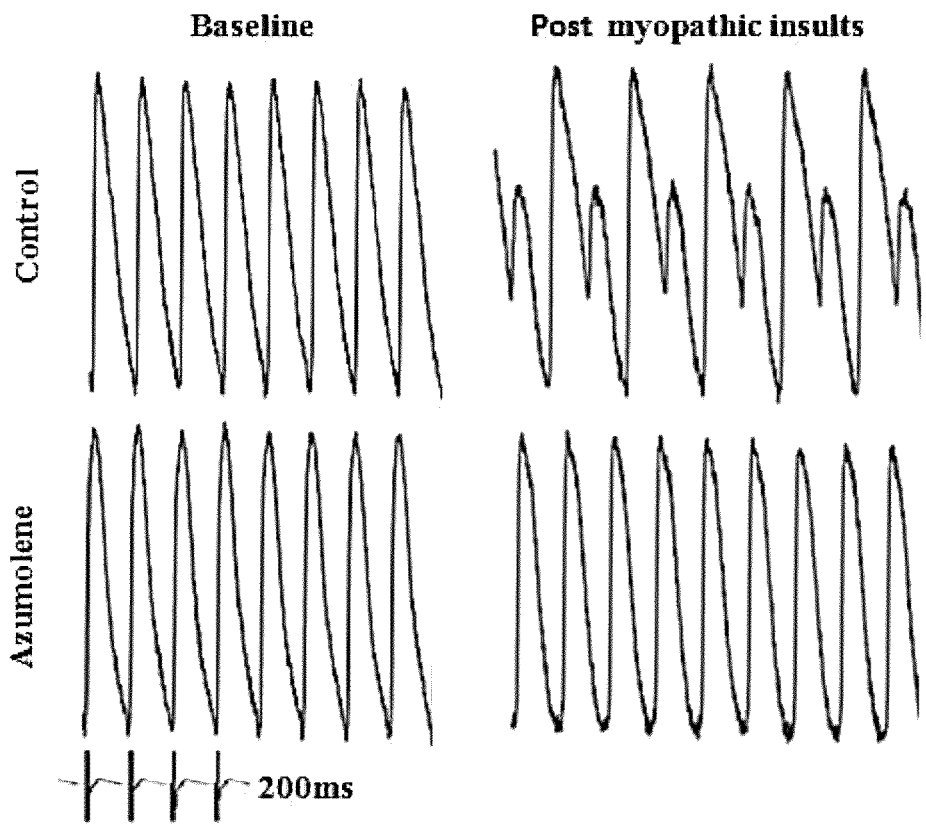
FIG. 7A is a series of tracings in azumolene-treated and untreated hearts at baseline and after inducement of myopathic insults.
Figure 7B:
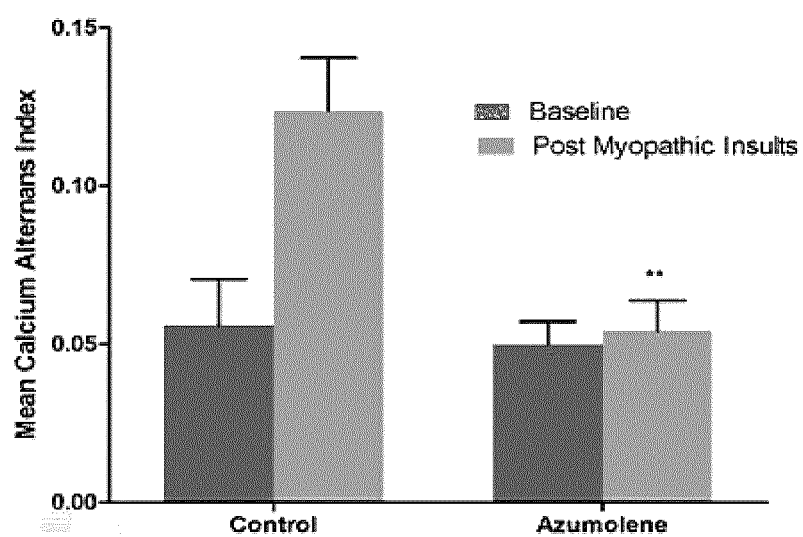
FIG. 7B is a graph showing the mean calcium alternans index in azumolene-treated and untreated hearts at baseline and after inducement of myopathic insults.
Figure 8B:
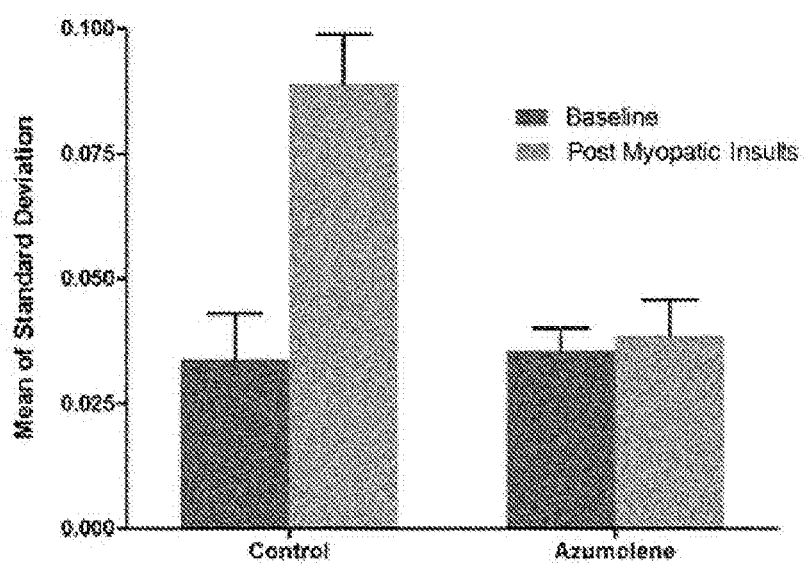
FIG. 8B is a graph showing the mean of standard deviation compared to azumolene-treated hearts post myopathic insults between control and azumolene-pretreated groups at baseline and post myopathic insults.
Figure 9A:
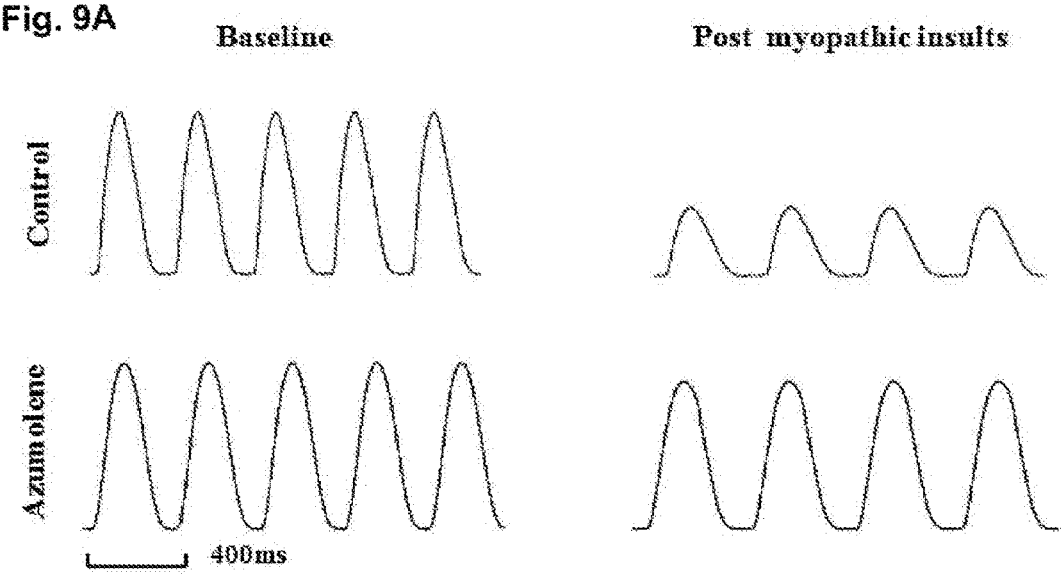
FIG. 9A is a series of tracings in control and azumolene-pretreated groups at baseline and post myopathic insults.
Figure 9B:
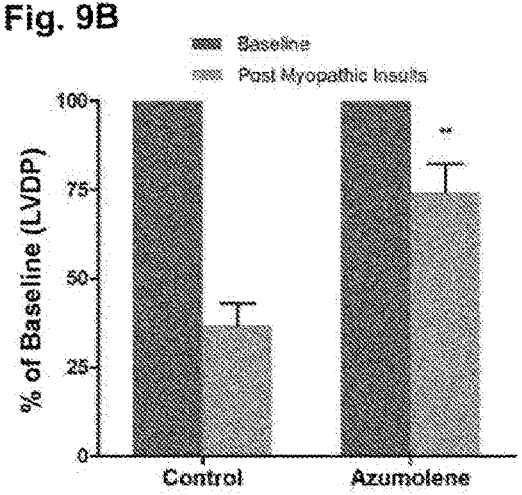
FIG. 9B is a graph showing % of baseline left ventricular developed pressure (LVDP) in control and azumolene-pretreated groups at baseline and following myopathic insults.
Figure 9C:
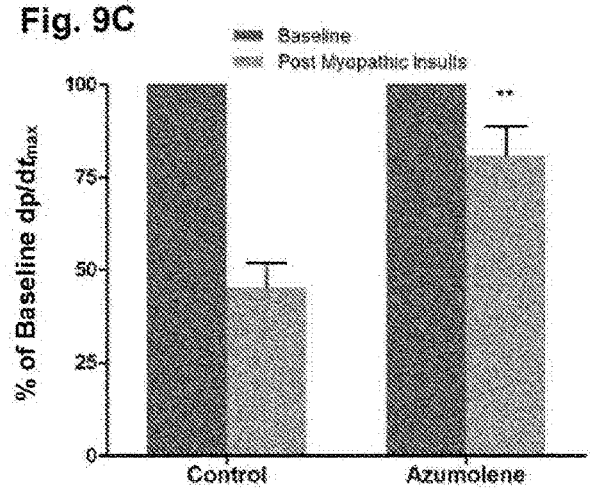
FIG. 9C is a graph showing % of baseline $dp/dt_{max}$ of control and azumolene-pretreated groups at baseline and following myopathic insults.

The effect of azumolene was further investigated. Optical mapping and left ventricular developed pressure (LVDP) were measured at baseline and following inducement of myopathic insults to the hearts (see FIGS. 6A and 6B). As shown in FIGS. 7A and 7B, the mean calcium alternans index of untreated-hearts increased significantly compared to azumolene-treated hearts. FIGS. 8A and 8B show the occurrence of spatial dyssynchronic in untreated compared to azumolene-treated hearts. Treatment with azumolene was found to reduce spatial calcium release dyssynchrony compared to untreated hearts (FIG. 8A) and further the mean of standard deviation was significantly increased in the control group post myopathic insults compared to the azumolene-treated group (FIG. 8B). Further pretreatment with azumolene significantly improved LVDP and $dp/dt_{max}$ following myopathic insults (FIGS. 9A, 9B and 9C).

Example 4: Safety of Chronic Modulation of Cardiac Ryanodine Receptor (RYR-2)

BACKGROUND: RYR-2 modulation is now proposed as an antiarrhythmic therapy. However, the safety of chronic RYR-2 modulation has not been established in regards to pro-arrhythmia and left ventricular (LV) function.

OBJECTIVE: Our aim in this study was to evaluate the effect of chronic use of RYR-2 modulation via dantrolene on electrical depolarization, and repolarization and LV function.

METHODS: We identified patients without known cardiac diseases who had 12-lead electrocardiograms (ECG), echo, Holter, or stress test performed during chronic oral dantrolene therapy (defined as >3 months use). All ECG and echo parameters were analyzed.

RESULTS: 20 patients (male=14) were included. Mean age was 65 (±9) years. 19 of the 20 patients had ECGs. All ECGs revealed sinus rhythm, and the mean heart rate was 67 (±14). Corrected QTc was 420 ms (±24). 2 patients had ECGs off dantrolene, and those didn't show any differences. The rest of the depolarization and repolarization parameters were within normal limits. LV size and function were normal in all studies assessed. Mean LV ejection fraction (LVEF) was 62% (±3%). 2 patients had Holter monitor, and 1 had a stress test. No major arrhythmia noted in the Holter or stress tests. Most of these patients used dantrolene for >5 years. No major cardiac events (life-threatening arrhythmia, sudden death, myocardial infarction) were documented during dantrolene therapy. See Table 1.

TABLE 1

| Total = 20 | Total |
|---|---|
| Age | 65 ± 9 |
| Male | 14 (78%) |
| PR | 173 ± 19 ms |
| QRS | 98 ± 10 ms |
| QTc | 420 ± 24 ms |
| JTc | 304 ± 79 ms |
| LVEF | 62 ± 3% |

CONCLUSIONS: Patients on chronic oral dantrolene did not have QRS or QTc prolongation, arrhythmia, pauses, or significant cardiac events. No detrimental effect noted on the LV systolic function.

Example 5: Safety of Chronic Cardiac Ryanodine Receptor Modulation: A 10-Year Experience Cardiac ryanodine receptors (RyR2) are crucial in calcium handling, and their dysfunction causes arrhythmias, contractile dysfunction, and heart failure [4], [7], [8]. Recently, dantrolene, a RyR-1 modulator, has been proven to modulate RyR-2, ameliorates arrhythmogenic calcium leak, and prevents nuclear translocation of cardiac CaM K-II preventing the development of cardiac hypertrophy [3]. Furthermore, dantrolene enhanced cardiac function in failing hearts [9] and improved short-term survival in ventricular arrhythmia [4]. However, much needed clinical trials in humans are lacking. To date, the cardiac safety of chronic RyR2 modulation in humans has not been evaluated. The safety of RyR2 modulation in patients who have had more than 10 years of RyR1 and RyR2 modulations by oral dantrolene is described herein for the first time.

Patients treated with chronic (>3 months) oral dantrolene, for muscle disorders, over the last 27 years in the Malignant Hyperthermia Clinic at Toronto General Hospital and without known cardiac disease, were screened. Patients who had an electrocardiogram or echocardiogram performed while on oral dantrolene were included. If more than 1 electrocardiogram and/or echocardiogram were available for any single patient, all were studied (to assess for any abnormality), but only the latest (with the longest therapy duration) was included in the analysis. Twenty patients (males, n=15) were included; at the time of the first cardiac test analyzed (either last electrocardiogram or last echocardiogram), mean age was 59±13 years, and mean therapy duration was 10.9±6 years. The median dose was 100 (interquartile ratio: 69 to 100) mg/d. Nineteen patients (95%) had electrocardiograms.

During a mean of 10.9±6 years follow-up of oral dantrolene, no major cardiac events (serious arrhythmia, sudden death, or myocardial infarction) were noted. All electrocardiograms revealed sinus rhythm. Mean QTc was 419±25 ms, and mean QRS duration was 97±10 ms. All conduction and repolarization parameters were within normal limits (Table 2). No dose-related QTc prolongation was noted. Four patients had serial electrocardiograms "on" and "off" dantrolene (either before dantrolene initiation or >3 weeks after stopping it). No changes between the electrocardiograms performed on and off dantrolene were observed (Table 2). Ten patients (50%) had at least 1 echocardiogram. All of those patients had normal left ventricular (LV) size and systolic function, mean ejection fraction 62±3%.

TABLE 2

Data Summary (N = 20)

| | |
|---|---|
| Age, mean ± SD, yrs | 59 ± 13 |
| Males | 15 (75) |
| Diabetes | 2 (10) |
| Hypertension | 3 (15) |
| Peripheral or cerebrovascular disease | 5 (25) |
| Malignant hyperthermia | 5 (25) |
| Duration of follow-up, mean ± SD, yrs | 10.9 ± 6 |
| Dose, median (IQR), mg | 100 (69 to 100) |
| Electrocardiogram | 19 (95) |
| Echocardiogram | 10 (50) |
| Heart rate, bpm, mean ± SD | 67 ± 13 |
| PR, ms, mean ± SD | 170 ± 20 |
| QRS, ms, mean ± SD | 97 ± 10 |
| QT, ms, mean ± SD | 401 ± 32 |
| QTc, ms, mean ± SD | 419 ± 25 |
| JTc, ms, mean ± SD | 322 ± 25 |
| Number of patients with PR >200 ms | 1 (5) (PR = 222 ms) |
| Number of patients with QTc >460 ms | 1 (5) (QTc = 465 ms in a woman) |
| LVEF, mean ± SD, % | 62 ± 3 |
| Patients with ECGs "on" and "off" dantrolene, n | 4 |
| Absolute change in average PR ± SD, ms (p value) | 12 ± 8 (p = 0.14) |
| PR "on" dantrolene, mean ± SD, ms | 178 ± 30 |
| PR "off" dantrolene, mean ± SD, ms | 169 ± 23 |
| Absolute change in average QRS ± SD, ms (p value) | 4 ± 3, (p = 0.71) |
| QRS "on" dantrolene, mean ± SD, ms | 97 ± 11 |
| QRS "off" dantrolene, mean ± SD, ms | 96 ± 15 |
| Absolute change in average QTc ± SD, ms (p value) | 12 ± 17, (p = 0.27) |
| QTc "on" dantrolene, mean ± SD, ms | 416 ± 13 |
| QTc "off" dantrolene, mean ± SD, ms | 405 ± 30 |

Values are n (%) unless otherwise stated
ECG = electrocardiogram; IQR = interquartile ratio; LVEF = left ventricular ejection fraction; PR = partial response.

Dantrolene's chronic use (orally) is rare, and this is believed to be the first study to report on long-term effects of RyR2 modulation and dantrolene use on cardiac activation and repolarization in humans. Therapeutic potentials for dantrolene when arrhythmia suppression is not satisfactory with current antiarrhythmic drugs, or when their side effects profile is not tolerable were observed. Evolving evidence suggests potential utility in ventricular arrhythmias and atrial fibrillation. An attractive, although underappreciated, aspect of dantrolene use is an automated antiarrhythmic paradigm, as the drug does not exert its therapeutic effect until the RyR2 receptors become dysfunctional, thus minimizing discernible effects on cardiac electrophysiology under basal states and providing favorable safety profile.

This study carries the inherent limitations of a retrospective design lacking the strengths of a study that would include data before and after dantrolene therapy. The data assessed patients with no underlying arrhythmia, that is, when RyR2 is not dysfunctional; dantrolene has no discernible proarrhythmic features. In a previous work [4], dantrolene did not affect the QT in an in vivo ventricular arrhythmia swine model. Although unlikely to be very different, potential proarrhythmic effects in humans cannot be ascertained from this data and further prospective studies (phase 1 and 2) are needed. Despite these limitations, it is believed that the present observational study provides initial safety data that will help researchers designing prospective crossover studies assessing the effect of dantrolene and/or RyR2 modulation on humans.

In conclusion, patients who had cardiac testing after 10 years of chronic dantrolene usage did not have QRS or QTc prolongation, and their left ventricular ejection fraction was normal. This observational data suggest that chronic RyR2 modulation can now be tested in prospective crossover studies to confirm these findings.

It should be appreciated that the exemplary embodiments of the present disclosure should not be construed to be limited to the examples that are now described; rather, the exemplary embodiments of the present disclosure should be construed to include any and all applications provided herein and all variations within the skill of the ordinary artisan.

REFERENCES

1. Li H, et al. Circ Heart Failure, 2015. Cardiac Resynchronization Therapy Reduces Subcellular Heterogeneity of Ryanodine Receptors, T-Tubules, and Ca2+ Sparks Produced by Dyssynchronous Heart Failure.
2. Aiba T et al. Circulation, 2009. Electrophysiological consequences of dyssynchronous heart failure and its restoration by resynchronization therapy
3. Gangopadhyay J P and Ikemoto N et al. Biochem Biophys Res Commun, 2010. Intracellular translocation of calmodulin and Ca2+/calmodulin-dependent protein kinase II during the development of hypertrophy in neonatal cardiomyocytes.
4. Zamiri N, et al. Circulation. 2014. Dantrolene improves survival after ventricular fibrillation by mitigating impaired calcium handling in animal models.
5. Kaye et al. Eur J Pharmacol. 2011. Augmentation of left ventricular mechanics by recirculation-mediated AAV2/1-SERCA2a gene delivery in experimental heart failure.
6. Hanna et al. Mol Pharmacol. 2014 October; 86(4): 438-449.
7. Fischer T H, et al. Circulation 2013; 128:970-981. Ca2+/calmodulin-dependent protein kinase II and protein kinase A differentially regulate sarcoplasmic reticulum Ca2+ leak in human cardiac pathology.

8. Dewenter M, et al. Circ Heart Fail 2017; 10(5):e003840. Calcium/calmodulin-dependent protein kinase II activity persists during chronic beta-adrenoceptor blockade in experimental and human heart failure.
9. Kobayashi S, et al. J Am Coll Cardiol 2009; 53:1993-2005. Dantrolene, a therapeutic agent for malignant hyperthermia, markedly improves the function of failing cardiomyocytes by stabilizing inter-domain interactions within the ryanodine receptor.

What is claimed is:

1. A method for treatment or prevention of a dyssynchronous cardiac dysfunction comprising chronically administering to a human patient in need thereof a therapeutically effective amount of dantrolene, or a derivative, an analog, or a solvate or hydrate thereof or a mixture of any of the foregoing.

2. The method of claim 1, wherein the patient is in need due to risk of cardiac dysfunction and the dantrolene, derivative, analog, solvate or hydrate or mixture thereof is administered before onset of the dyssynchronous cardiac dysfunction.

3. The method of claim 1, wherein the patient is in need due to risk of cardiac dysfunction and the dantrolene, derivative, analog, solvate or hydrate of mixture thereof is administered before and after onset of the dyssynchronous cardiac dysfunction or is administered during or immediately following detection of the dyssynchronous cardiac dysfunction.

4. The method of claim 1, wherein the dyssynchronous cardiac dysfunction is a non-arrhythmia cardiac dysfunction.

5. The method of claim 4, wherein the non-arrhythmia cardiac dysfunction is selected from heart failure, cardiomyopathy, ischemia induced cardiomyopathy, ischemia, chemotherapy, pacing induced cardiomyopathy or ion channel mutation related dysfunction.

6. The method of claim 1, wherein the dyssynchronous cardiac dysfunction is chemotherapy induced cardiomyopathy or viral myocarditis.

7. The method of claim 1, wherein the dyssynchronous cardiac dysfunction is associated with calcium alternans or the patient is in need due to a past, present, or planned course of chemotherapy.

8. The method of claim 1, wherein the patient has no history of dyssynchronous cardiac dysfunction.

9. The method of claim 1, wherein the patient has been identified to be suitable for installation of a left ventricular assistive device or a cardiac contractility modulation (CCM) device.

10. The method according to claim 1, wherein the dantrolene, derivative, analog, solvate or hydrate or mixture thereof is or comprises dantrolene sodium.

11. The method according to claim 1, wherein the dantrolene analog is or comprises azumolene, optionally the pharmaceutically acceptable salt azumolene sodium.

12. The method according to claim 1, wherein the therapeutically effective amount of dantrolene, derivative, analog, solvate or hydrate or mixture thereof is from 0.1 µg/kg/day to about 1000 mg/kg/day, optionally about 2.5 mg/kg/day, about 5 mg/kg/day, about 10 mg/kg/day, about 15 mg/kg/day, about 20 mg/kg/day, about 25 mg/kg/day, about 30 mg/kg/day, about 35 mg/kg/day, about 40 mg/kg/day, about 45 mg/kg/day or about 50 mg/kg/day.

13. The method according to claim 1, wherein the amount administered is effective for improving calcium temporal dyssynchrony, improving calcium spatial dyssynchrony, improving defibrillation success, improving hemodynamic performance, improving sinus rhythm after defibrillation, improving sustained return of spontaneous circulation (ROSC), reducing of time to ROSC, improving systolic blood pressure, improving diastolic blood pressure, improving diastolic function, improving cardiac contractility, reducing calcium amplitude alternans (CaA-ALT), reducing RyR2 hyperphosphorylation, reducing RyR2 calcium leak, increasing resistance to VF induction, improved survival or a combination thereof.

14. The method of claim 1, wherein the dantrolene, or derivative, analog, solvate or hydrate or mixture thereof is administered in a pharmaceutical composition, optionally a pharmaceutical composition further comprising a carrier.

15. The method of claim 14, wherein the pharmaceutical composition is in a dosage form selected from a solid dosage form and a liquid dosage form.

16. The method of claim 14, wherein the pharmaceutical composition is administered by parenteral, intravenous, subcutaneous, intracardial, intramuscular, or oral administration.

17. The method of claim 16, wherein the pharmaceutical composition is an injectable dosage form.

18. The method of claim 17, wherein the injectable dosage form is a subcutaneous depot injection form.

19. A method for resynchronizing cardiac calcium levels in a patient the method comprising chronically administering to a patient in need thereof a therapeutically effective amount of dantrolene, or a derivative, an analog, or a solvate or hydrate thereof or a mixture of any of the foregoing.

20. A method for treatment of dyssynchronous diastolic uptake and release dysfunction due to calcium leakage wherein spatial discordance and/or calcium transients are resynchronized, comprising administering to a patient in need thereof a therapeutically effective amount of dantrolene, or a derivative, an analog, a solvate or hydrate thereof or a mixture of any of the foregoing.

* * * * *